US011278673B2

(12) United States Patent
Chang et al.

(10) Patent No.: US 11,278,673 B2
(45) Date of Patent: Mar. 22, 2022

(54) RECORDING DEVICE FOR INJECTION DEVICE

(71) Applicant: Quanta Computer Inc., Taoyuan (TW)

(72) Inventors: Chia-Yuan Chang, Taoyuan (TW); Jung-Wen Chang, Taoyuan (TW); Chin-Kang Chang, Taoyuan (TW); Chao-Ching Huang, Taoyuan (TW)

(73) Assignee: QUANTA COMPUTER INC., Taoyuan (TW)

( * ) Notice: Subject to any disclaimer, the term of this patent is extended or adjusted under 35 U.S.C. 154(b) by 279 days.

(21) Appl. No.: 16/594,468

(22) Filed: Oct. 7, 2019

(65) Prior Publication Data
US 2021/0008286 A1    Jan. 14, 2021

(30) Foreign Application Priority Data
Jul. 12, 2019   (TW) ................................. 108124761

(51) Int. Cl.
*A61M 5/31* (2006.01)
*G02B 5/04* (2006.01)
*A61M 5/315* (2006.01)

(52) U.S. Cl.
CPC ...... *A61M 5/3135* (2013.01); *A61M 5/31525* (2013.01); *G02B 5/04* (2013.01)

(58) Field of Classification Search
CPC ............ A61M 5/3135; A61M 5/31525; A61M 2205/3306; A61M 2205/502; G02B 5/04
See application file for complete search history.

(56) References Cited

U.S. PATENT DOCUMENTS

| 2015/0032059 A1* | 1/2015 | Allerdings ........ A61M 5/31525 604/189 |
| 2018/0304017 A1 | 10/2018 | Edwards et al. |

FOREIGN PATENT DOCUMENTS

| CN | 103648555 A | 3/2014 |
| CN | 104220116 A | 12/2014 |
| CN | 108917678 A | 11/2018 |
| CN | 109689135 A | 4/2019 |
| WO | 2016171818 A1 | 10/2016 |
| WO | 2018184785 A1 | 10/2018 |

OTHER PUBLICATIONS

Office Action in China Patent Application Serial No. 201910687393.0 including English Translation, dated Jan. 4, 2022.

* cited by examiner

*Primary Examiner* — Bradley J Osinski

(57) ABSTRACT

A recording device for injection device includes a housing, a viewing window, a photographic module, a light splitting element and a signal transmission device. The housing is removably mounted on a dose scale window of an injection device. The viewing window is formed on a surface of the housing, and a viewing path is formed from the viewing window to the dose scale window. The photographic module is located on the housing, and provided with an image-capturing optical axis which is perpendicular to the viewing path. The light splitting element is located at an intersection of the viewing path and the image-capturing optical axis for guiding information located in the dose scale window to the photographic module and the viewing window, respectively. The signal transmission device is electrically connected to the photographic module for transmitting signals of the photographic module to an external device.

10 Claims, 4 Drawing Sheets

RECORDING DEVICE FOR INJECTION DEVICE

RELATED APPLICATIONS

This application claims priority to Taiwan Application Serial Number 108124761, filed Jul. 12, 2019, which is herein incorporated by reference.

BACKGROUND

Field of Disclosure

The disclosure relates to a recording device. More particularly, the disclosure relates to a recording device for injection device.

Description of Related Art

In general, since diabetic patients need to inject insulin for the treatment of diabetes once or several times per day, most of them prefers to use a disposable insulin pen which is pre-filled therein so as to inject insulin to the body on their own.

Furthermore, for self-management of health, an auxiliary method provided by related industries is to mount an image sensing device on a disposable insulin pen such that the image sensing device covers a dose scale window of the disposable insulin pen. Thus, the image sensing device captures the dose image from the dose scale window.

However, since the image sensing device totally covers the dose scale window of the disposable insulin pen to visually block the dose scale window, a user of the disposable insulin pen can only remove the image sensing device for reading the dose value from the dose scale window of the disposable insulin pen, thereby, causing many inconveniences and troubles, and reducing the user's willingness to use.

SUMMARY

In one embodiment of the disclosure, a recording device for injection device is provided, and the recording device includes a housing, a viewing window, a photographic module, a light splitting element and a signal transmission device. The housing is removably mounted on a dose scale window of an injection device. The viewing window is formed on a surface of the housing, and a viewing path is formed from the viewing window to the dose scale window. The photographic module is located on the housing, and provided with an image-capturing optical axis which is perpendicular to the viewing path. The light splitting element is located at an intersection of the viewing path and the image-capturing optical axis so as to simultaneously guide information located in the dose scale window to the photographic module and the viewing window, respectively. The signal transmission device is electrically connected to the photographic module for transmitting signals of the photographic module to an external device.

According to one or more embodiments of the disclosure, in the recording device for injection device, the housing includes a longitudinal passage that is disposed opposite to the viewing window for receiving the injection device. A long axis direction of the longitudinal passage and a long axis direction of the viewing path are orthogonal to each other.

According to one or more embodiments of the disclosure, in the recording device for injection device, the housing includes an engaging sheath that is disposed within the longitudinal passage for removably engaging with one syringe of the injection device.

According to one or more embodiments of the disclosure, in the recording device for injection device, the housing includes a receiving space. The receiving space is disposed between the longitudinal passage and the viewing window to connect to the longitudinal passage and the viewing window for receiving the light splitting element, the photographic module and the signal transmission device. The photographic module is located away from the viewing path.

According to one or more embodiments of the disclosure, in the recording device for injection device, the light splitting element includes a triangular prism.

According to one or more embodiments of the disclosure, in the recording device for injection device, the light splitting element includes a transflective optical sheet provided with a flat glass and an optical coating film formed on one surface of the flat glass. A transmittance rate and a reflection rate of the optical coating film are 50%, respectively.

According to one or more embodiments of the disclosure, in the recording device for injection device, the photographic module is provided with a short-focus lens, and the image-capturing optical axis of the short-focus lens passes through the light splitting element.

According to one or more embodiments of the disclosure, in the recording device for injection device, the injection device is an insulin injection pen having an injection needle and an injection button at two opposite ends thereof, respectively. The housing is removably sleeved on one of the two opposite ends of the insulin injection pen being neighboring to the injection button.

According to one or more embodiments of the disclosure, the recording device for injection device further includes a processing unit. The processing unit is disposed on the housing, electrically connected to the photographic module and the signal transmission device, and used to reverse an inverted image captured by the photographic module to a non-inverted image before the signals of the photographic module are transmitted to the external device.

In another embodiment of the disclosure, a recording device for injection device is provided, and the recording device includes a housing, an engaging sheath, an opening, a viewing window, a photographic module, a light splitting element and a signal transmission device. The housing is provided with a first side and a second side which are opposite to each other. The engaging sheath is disposed on the first side of the housing for engaging with an injection device. The opening is disposed on the first side of the housing, and aligned with the injection device. The viewing window is disposed on the second side of the housing. The photographic module is located on the housing. The light splitting element is received in the housing, disposed between the opening and the viewing window, and used to simultaneously guide lights travelled from the opening to the photographic module and the viewing window, respectively. The signal transmission device is electrically connected to the photographic module for transmitting signals of the photographic module to an external device.

Thus, through the construction of the embodiments above, not only the information located in the dose scale window can be sent to a control end (e.g., a mobile phone or a cloud server), but also the information located in the dose scale window can be visually observed by a user, thereby solving the above inconvenience and trouble, and improving the user's willingness to use.

The above description is merely used for illustrating the problems to be resolved, the technical methods for resolving the problems and their efficacies, etc. The specific details of the disclosure will be explained in the embodiments below and related drawings.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure. In the drawings.

DESCRIPTION OF THE EMBODIMENTS

Figure 1:
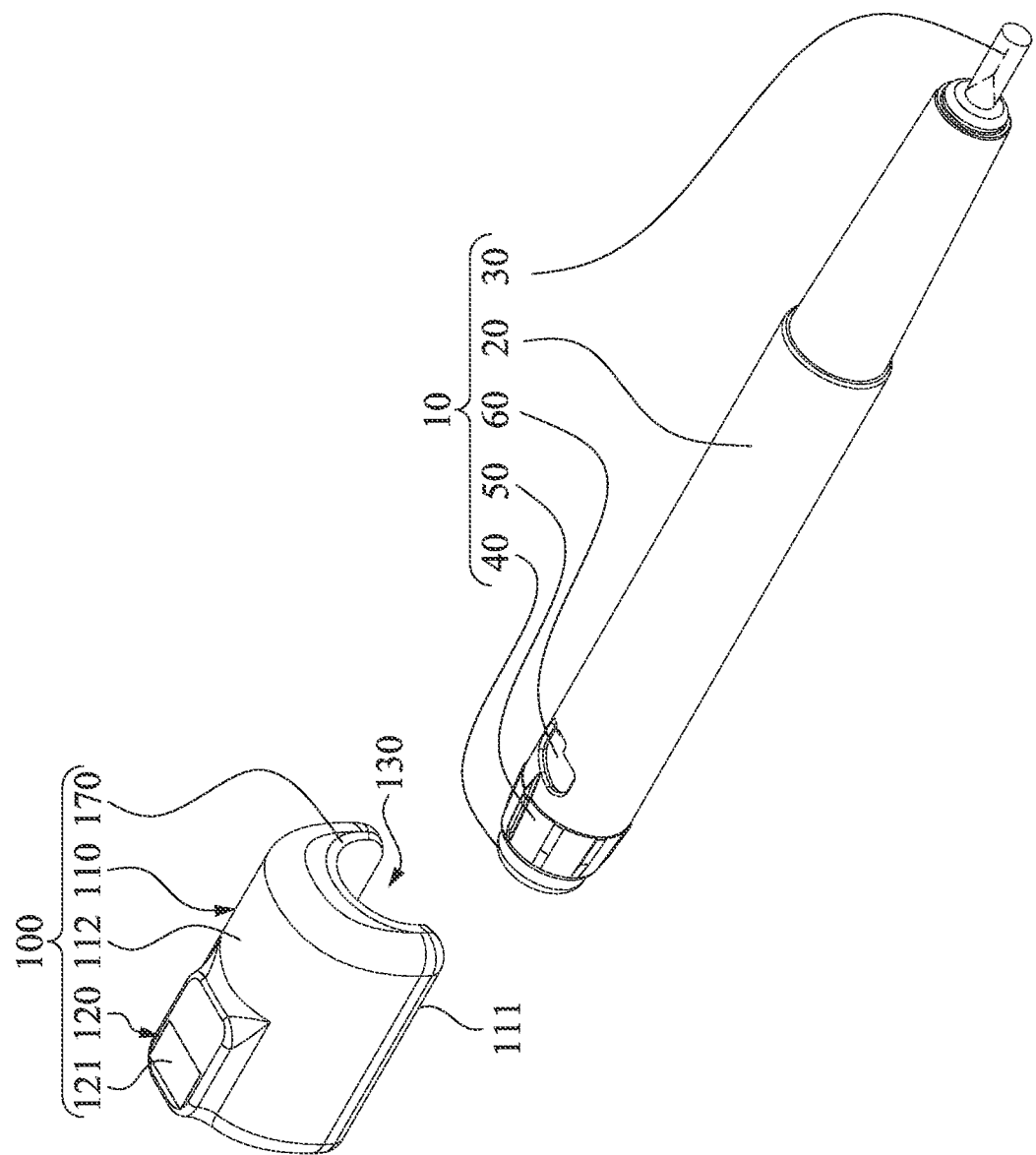
FIG. 1 is an exploded view of an insulin injection pen and a recording device according to one embodiment of the disclosure.

Reference will now be made in detail to the present embodiments of the disclosure, examples of which are illustrated in the accompanying drawings. Wherever possible, the same reference numbers are used in the drawings and the description to refer to the same or like parts. According to the embodiments, it will be apparent to those skilled in the art that various modifications and variations can be made to the structure of the disclosure without departing from the scope or spirit of the disclosure.

Reference is now made to FIG. 1, in which FIG. 1 is an exploded view of an insulin injection pen 10 and a recording device 100 according to one embodiment of the disclosure. As shown in FIG. 1, the recording device is used to be assembled on an injection device for being operated to record the dose of the injection device for injection each time. Briefly, the injection device includes a syringe 20, an injection needle 30, an injection button 40, a dose selection knob 50 and a dose scale window 60. The injection needle 30 and the injection button 40 are disposed at two opposite ends of the syringe 20, respectively. The injection button 40 can simultaneously push the injection material (not shown) that is filled in the syringe 20 outwards from the syringe 20 through the injection needle 30 after pressing the injection button 40. The dose scale window 60 is located at one end of the syringe 20 neighboring to the injection button 40, and is exposed outwards from an outer surface of the syringe 20 to exactly express information such as a dose scale value. The dose selection knob 50 is located at one end of the syringe 20 neighboring to the injection button 40 for rotating the dose scale within the dose scale window 60. In this embodiment, for example, the injection device is an insulin injection pen 10. Since the insulin injection pen 10 is a conventional device, it will not be described again hereinafter. However, the disclosure is not limited to use on an insulin injection pen 10 only.

Figure 2:
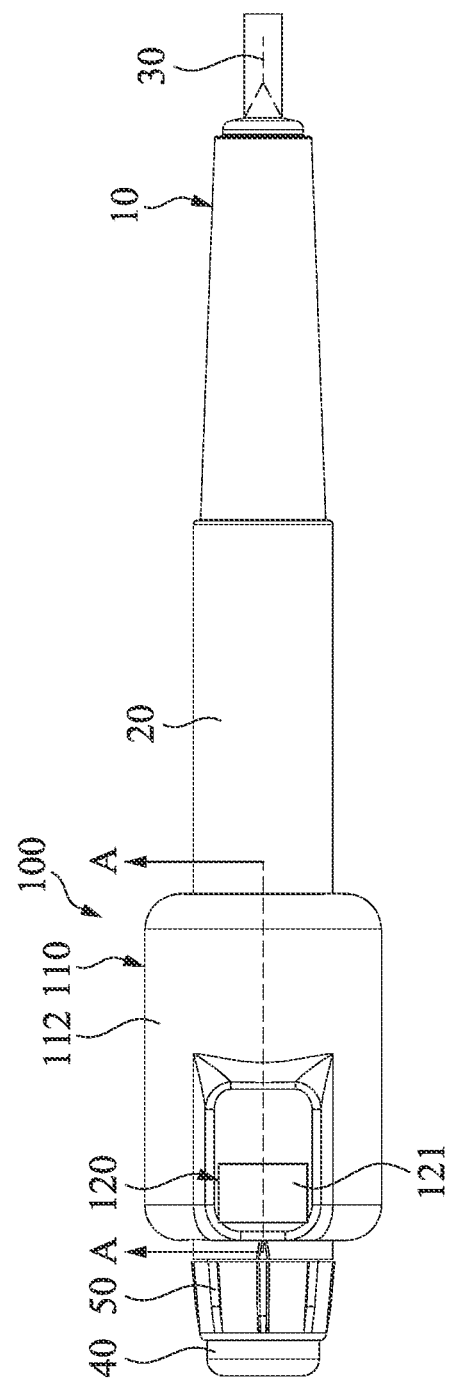
FIG. 2 is an assembling view of the recording device of FIG. 1.
Figure 3:
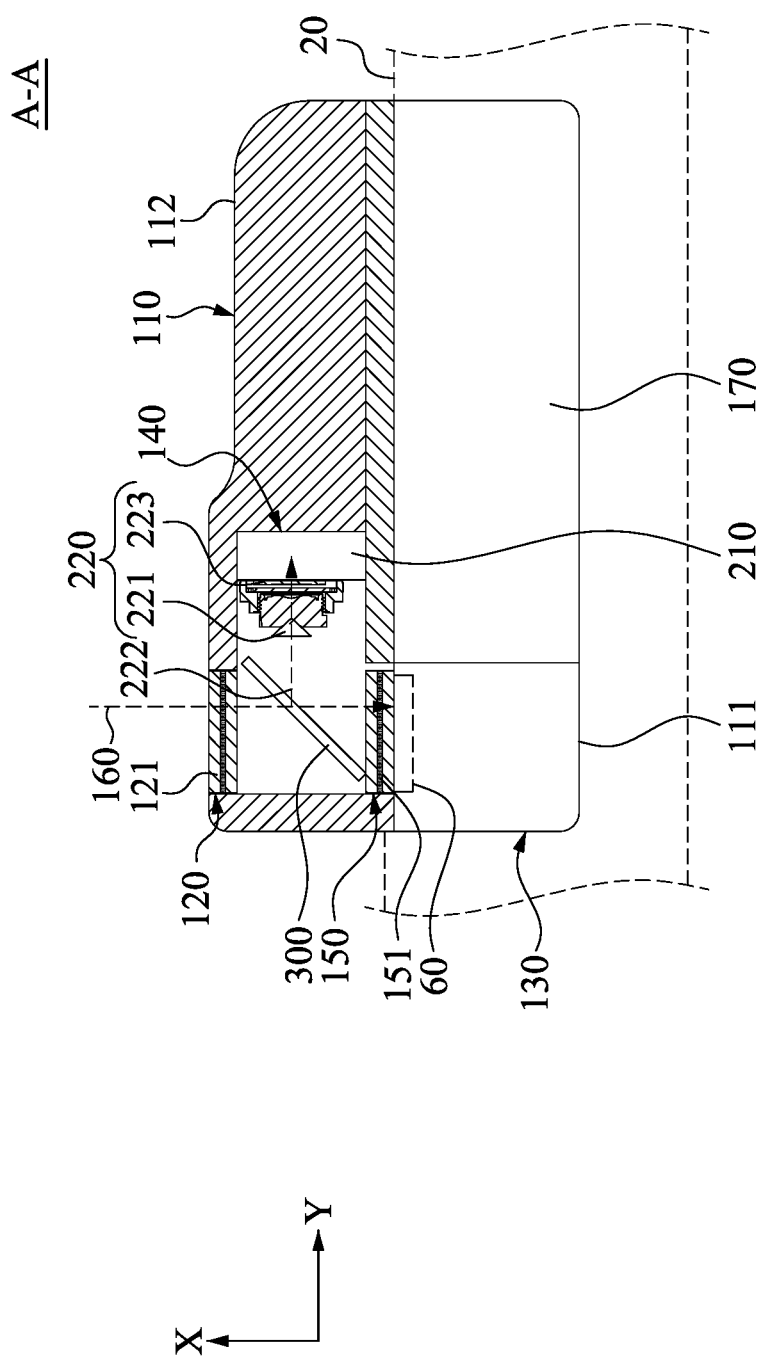
FIG. 3 is a partial cross-sectional view taken along a line A-A of FIG. 2.

Reference is now made to FIG. 2 and FIG. 3, in which FIG. 2 is an assembling view of the recording device of FIG. 1, and FIG. 3 is a partial cross-sectional view taken along a line A-A of FIG. 2. As shown in FIG. 2 and FIG. 3, the recording device 100 includes a housing 110, a viewing window 120, a photographic module 220 and a light splitting element 300. The housing 110 is removably assembled on the syringe 20 of the insulin injection pen 10, especially, is positioned on the dose scale window 60 of the insulin injection pen 10. The viewing window 120 is formed on an outer surface of the housing 110 being opposite to the insulin injection pen 10, and a viewing path 160 is formed from the viewing window 120 to the dose scale window 60. The viewing path 160 is a light traveling path, and the long axis direction of the viewing path 160 (e.g., X-axis direction) intersects with the long axis direction of the syringe 20 (e.g., Y-axis direction), and is even perpendicular to the long axis direction of the syringe 20 (e.g., Y-axis direction). That is, whether seeing through any media (e.g., glass cover) or not, the user can see the dose scale window 60 of the insulin injection pen 10 from the viewing window 120 of the housing 110. The photographic module 220 is located on the housing 110, and provided with a lens unit 221 and a photosensitive element 223. The lens unit 221 is optically coupled with the photosensitive element 223, and the lens unit 221 has an image-capturing optical axis 222. The image-capturing optical axis 222 is parallel to the long axis direction of the syringe 20 (e.g., Y-axis direction), and the image-capturing optical axis 222 is intersected by the long axis direction of the viewing path 160 (e.g., X-axis direction), or the image-capturing optical axis 222 even is perpendicular to the long axis direction of the viewing path 160 (e.g., X-axis direction). Also, the image-capturing optical axis 222 passes through the photosensitive element 223. The light splitting element 300 is fixedly coupled in the housing 110, and is located at an intersection of the viewing path 160 and the image-capturing optical axis 222, that is, the image-capturing optical axis 222 of the lens unit 221 and the viewing path 160 of the viewing window 120 respectively pass through the light splitting element 300. For example, the lens unit 221 is provided with a short-focus lens, and the light splitting element 300 includes a triangular prism. However, the disclosure is not limited to types of the lens unit 221 and the light splitting element 300.

Accordingly, since the information located in the dose scale window 60 can be simultaneously guided to the photographic module 220 and the viewing window 120 by the light splitting element 300, respectively, when the recording device 100 is activated, not only the information (e.g., dose scale) located in the dose scale window 60 can be recorded, but also the information (e.g., dose scale) within the dose scale window 60 can be visually observed by a user at the same time. Therefore, the information (e.g., dose scale) within the dose scale window 60 can be confirmed without removing the recording device 100 away from the dose scale window 60 of the insulin injection pen 10.

More specifically, the housing 110 is formed with a first side 111 and a second side 112 which are opposite to each other. The housing 110 is formed with a longitudinal passage 130. The longitudinal passage 130 and the viewing window 120 are oppositely arranged on the first side 111 and the second side 112, respectively. The longitudinal passage 130 can receive the insulin injection pen 10 therein. The long axis direction (e.g., Y-axis direction) of the longitudinal passage 130 and the long axis direction of the viewing path 160 (e.g., X-axis direction) are orthogonal to each other. Furthermore, the housing 110 includes an engaging sheath 170 that is located on the first side 111 of the housing 110, and the engaging sheath 170 is fixedly disposed within the longitudinal passage 130 for removably engaging with the syringe 20 of the insulin injection pen 10. For example, the longitudinal passage 130 is semi-circular, and the cross-section of the engaging sheath 170 is C-shaped, such that the syringe 20 located in the longitudinal passage 130 can be rotated relative to the housing 110. However, the disclosure is not limited thereto, and in other embodiments, the cross-section of the engaging sheath may also be O-shaped.

Furthermore, in the embodiment, the housing 110 further includes a receiving space 140 that is disposed between the longitudinal passage 130 and the viewing window 120 to connect to the longitudinal passage 130 and the viewing window 120. One end of the receiving space 140 is connected to the viewing window 120, and the other end of the receiving space 140 is connected to the longitudinal passage 130 through an opening 150. The opening 150 is formed on the first side 111 of the housing 110, and is aligned with the insulin injection pen 10. The receiving space 140 mutually receives the light splitting element 300 and the photographic module 220, and the photographic module 220 is located away from the viewing path 160, or not located on the viewing path 160. The light splitting element 300 is disposed between the opening 150 and the viewing window 120, and is used to simultaneously direct lights travelled from the opening 150 to the photographic module 220 and the viewing window 120, respectively. The housing 110 seals the opening 150 through a light-transmitting plate 151, and seals the viewing window 120 through another light-transmitting plate 121. However, the disclosure is not limited to that the light-transmitting plates 121 and 151 must be presence.

Figure 4:
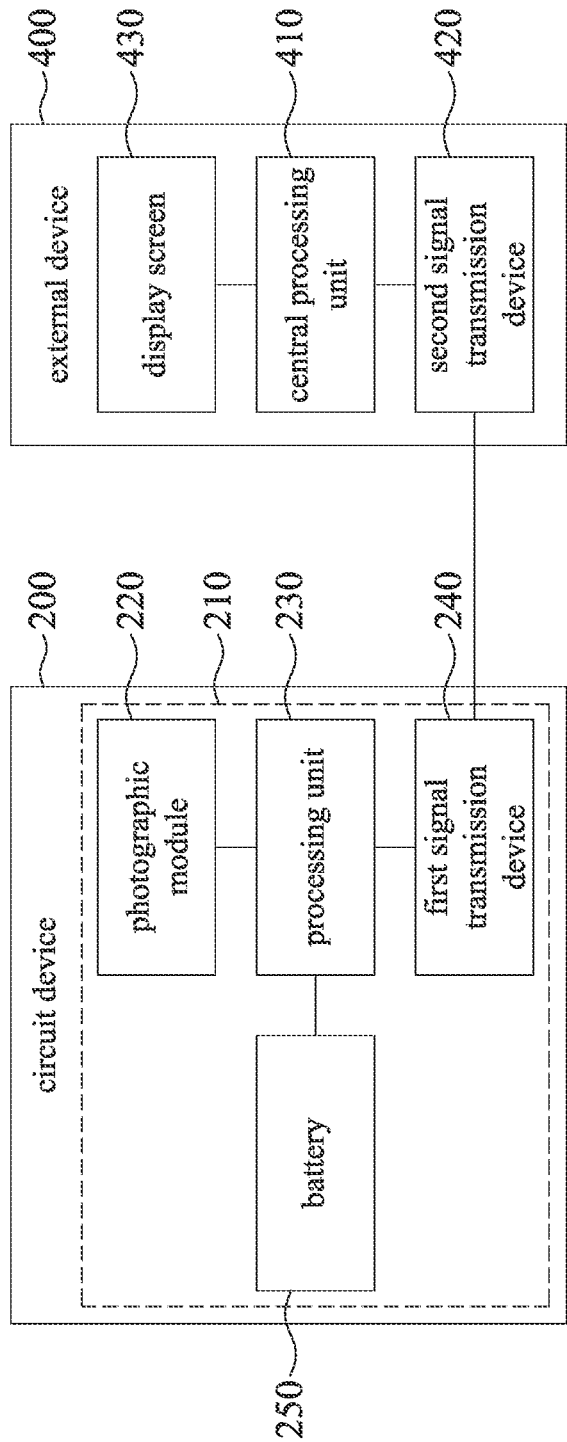
FIG. 4 is a block diagram of an external device and a recording device according to one embodiment of the disclosure.

Reference is now made to FIG. 3 and FIG. 4, in which FIG. 4 is a block diagram of an external device 400 and a recording device 100 according to one embodiment of the disclosure. As shown in FIG. 3 and FIG. 4, the recording device 100 further includes a first signal transmission device 240. The first signal transmission device 240 is disposed in the housing 110, and electrically connected to the photographic module 220 for transmitting signals of the photographic module 220 to an external device 400. Specifically, the external device 400 is another device other than the recording device 100, and the external device 400 includes a central processing unit 410, a second signal transmission device 420 and a display screen 430. The central processing unit 410 is electrically connected to the second signal transmission device 420 and the display screen 430.

Therefore, when the recording device 100 is activated to instruct the photographic module 220 to photography information located in the dose scale window 60, the first signal transmission device 240 transmits the information located in the dose scale window 60 to the second signal transmission device 420 of the external device 400. Thus, by the operation of the central processing unit 410, a user can obtain entire related information from the display screen 430 of the external device 400. For example, the external device 400 is, for example, one of a smart phone, a cloud server and the like, and the second signal transmission device is, for example, a blue tooth transmission device or a WIFI transmission device or the like.

In addition, the recording device 100 further includes a processing unit 230. The processing unit 230 is disposed on the housing 110, electrically connected to the photographic module 220 and the first signal transmission device 240, and the processing unit 230 is used to perform an image reversal procedure as to reverse an inverted image captured by the photographic module 220 to a non-inverted image. Since the lens unit 221 obtains the inverted image through the light splitting element 300, the image captured by the photographic module 220 can be processed to reverse the inverted image to a non-inverted image by the processing unit 230 before the signals are transmitted to the external device 400.

However, other than performing the image reversal procedure on the image captured by the photographic module through hardware, the disclosure is not limited to performing the image reversal procedure on the image captured by the image reversal procedure through the firmware or the software. In addition, in other embodiments, the disclosure can also perform the image reversal procedure on the image captured by the photographic module through hardware (e.g., central processing unit 410), firmware or software of the external device 400.

In this embodiment, the photographic module 220, the processing unit 230, the first signal transmission device 240 and the battery 250 are all mounted on a circuit board 210, and are electrically connected to each other through the circuit board 210. Therefore, the photographic module 220, the processing unit 230, the first signal transmission device 240, the battery 250 and the circuit board 210 are mutually integrated as a circuit device 200 that is fixedly installed within the receiving space 140.

Thus, when a user would like to inject with the insulin injection pen 10 cooperating with the recording device 100, the user sequentially performs with the following steps. First, the recording device 100 is activated; then, an application of the external device 400 is executed, such that the second signal transmission device 420 of the external device 400 can wirelessly connect with the first signal transmission device 240 of the recording device 100; next, the dose selection knob 50 of the insulin injection pen 10 is rotated to adjust the applied dose (i.e., dose scale in the dose scale window 60); then, a determination is made to whether the dose scale in the dose scale window 60 meets an expecting dose predetermined in the application of the external device 400; and the information located in the dose scale window 60 is recorded by the photographic module 220, and transmitted back to the external device 400 after the injection button 40 is pushed.

It is noted, regardless of whether the information located in the dose scale window 60 is being recorded by the photographic module 220, the above structure allows the user to directly observe the dose scale through the viewing window 120, and directly confirms whether the dose to be applied for injection meets an expecting dose predetermined in the application of the external device 400 so that the recording device 100 is not needed to be removed away from the dose scale window 60 of the insulin injection pen 10.

Figure 5:
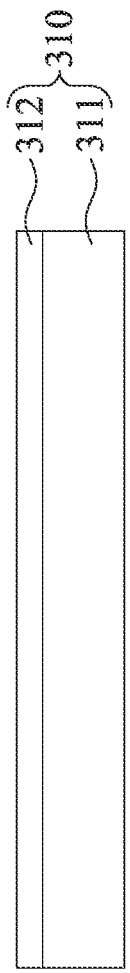
FIG. 5 is a side view of a light splitting element according to one embodiment of the disclosure.

FIG. 5 is a side view of a light splitting element 301 according to one embodiment of the disclosure. As shown in FIG. 5, in another embodiment, the light splitting element 301 is a transflective optical sheet 310 rather than a triangular prism. The transflective optical sheet 310 includes a flat glass 311 and an optical coating film 312 formed on one surface of the flat glass 311. A transmittance rate and a reflection rate of the optical coating film are 50%, respectively.

Although the disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the disclosure without departing from the scope or spirit of the disclosure. In view of the foregoing, it is intended that the disclosure cover modifications and variations of this disclosure provided they fall within the scope of the following claims and their equivalents.

What is claimed is:

1. A recording device for an injection device, comprising:
   a housing that is removably mounted on a dose scale window of the injection device;
   a viewing window that is formed on a surface of the housing, wherein a viewing path is formed from the viewing window to the dose scale window;
   a photographic module that is located on the housing, and provided with an image-capturing optical axis which is perpendicular to the viewing path;
   a light splitting element that is located at an intersection of the viewing path and the image-capturing optical axis so as to simultaneously guide information located in the dose scale window to the photographic module and the viewing window, respectively; and
   a signal transmission device that is electrically connected to the photographic module for transmitting signals of the photographic module to an external device.

2. The recording device for the injection device of claim 1, wherein the housing comprises a longitudinal passage that is disposed opposite to the viewing window, and the longitudinal passage is used to receive the injection device, wherein a long axis direction of the longitudinal passage and a long axis direction of the viewing path are orthogonal to each other.

3. The recording device for the injection device of claim 2, wherein the housing comprises an engaging sheath that is disposed within the longitudinal passage for removably engaging with one syringe of the injection device.

4. The recording device for the injection device of claim 2, wherein the housing comprises:
   a receiving space that is disposed between the longitudinal passage and the viewing window and connected to the longitudinal passage and the viewing window, for receiving the light splitting element, the photographic module and the signal transmission device, wherein the photographic module is located away from the viewing path.

5. The recording device for the injection device of claim 1, wherein the light splitting element comprises a triangular prism.

6. The recording device for the injection device of claim 1, wherein the light splitting element comprises a transflective optical sheet, and the transflective optical sheet is provided with a flat glass and an optical coating film formed on one surface of the flat glass, wherein a transmittance rate and a reflection rate of the optical coating film are 50%, respectively.

7. The recording device for the injection device of claim 1, wherein the photographic module is provided with a short-focus lens, and the image-capturing optical axis of the short-focus lens passes through the light splitting element.

8. The recording device for the injection device of claim 1, wherein the injection device is an insulin injection pen having an injection needle and an injection button at two opposite ends thereof, respectively, wherein the housing is removably sleeved on one of the two opposite ends of the insulin injection pen adjacent to the injection button.

9. The recording device for the injection device of claim 1, further comprising:
   a processing unit that is disposed on the housing, electrically connected to the photographic module and the signal transmission device, and used to reverse an inverted image captured by the photographic module to a non-inverted image before the signals of the photographic module are transmitted to the external device.

10. A recording device for an injection device, comprising:
    a housing having a first side and a second side which are opposite to each other;
    an engaging sheath that is disposed on the first side of the housing for engaging with an injection device;
    an opening that is formed on the first side of the housing, and aligned with the injection device;
    a viewing window that is disposed on the second side of the housing;
    a photographic module that is located on the housing;
    a light splitting element that is received in the housing, disposed between the opening and the viewing window, and used to simultaneously guide lights travelling from the opening to the photographic module and the viewing window, respectively; and
    a signal transmission device that is electrically connected to the photographic module for transmitting signals of the photographic module to an external device.

* * * * *